United States Patent
Lerch et al.

(10) Patent No.: US 10,653,370 B2
(45) Date of Patent: May 19, 2020

(54) SYSTEM WITH A GANTRY AND A RADIATION PROTECTION BOOTH AND METHOD FOR OPERATING A MEDICAL IMAGING APPARATUS

(71) Applicant: Siemens Healthcare GmbH, Erlangen (DE)

(72) Inventors: Daniel Lerch, Weilersbach (DE); Matthias May, Erlangen (DE); Carsten Thierfelder, Pinzberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 98 days.

(21) Appl. No.: 15/805,266

(22) Filed: Nov. 7, 2017

(65) Prior Publication Data

US 2018/0146933 A1 May 31, 2018

(30) Foreign Application Priority Data

Nov. 25, 2016 (DE) .......................... 10 2016 223 490

(51) Int. Cl.
| | |
|---|---|
| *A61B 90/00* | (2016.01) |
| *G21F 7/00* | (2006.01) |
| *A61B 6/10* | (2006.01) |
| *A61B 6/03* | (2006.01) |
| *A61B 6/00* | (2006.01) |

(Continued)

(52) U.S. Cl.
CPC .............. *A61B 6/107* (2013.01); *A61B 6/032* (2013.01); *A61B 6/035* (2013.01); *A61B 6/4405* (2013.01); *A61B 6/4476* (2013.01); *A61B 6/54* (2013.01); *A61B 6/56* (2013.01); *A61B 17/3211* (2013.01); *A61B 17/320016* (2013.01); *A61B 34/30* (2016.02); *A61B 90/00* (2016.02); *A61N 5/1077* (2013.01); *G21F 7/00* (2013.01); *A61B 6/4435* (2013.01); *A61B 2034/301* (2016.02); *A61B 2090/376* (2016.02); *A61B 2090/3762* (2016.02)

(58) Field of Classification Search
CPC ........... A61B 6/032; A61B 6/56; A61B 6/035; A61B 6/037; A61B 6/4405; A61B 6/107; A61B 6/4035; A61B 6/4476; A61B 2090/3762; A61B 90/00; A61B 6/10
See application file for complete search history.

(56) References Cited

U.S. PATENT DOCUMENTS

| | | |
|---|---|---|
| 5,097,497 A | 3/1992 | Deucher |
| 6,653,648 B2 | 11/2003 | Goldstein |

(Continued)

FOREIGN PATENT DOCUMENTS

| | | |
|---|---|---|
| DE | 69124985 T2 | 6/1997 |
| DE | 102014226467 A1 | 6/2016 |

(Continued)

OTHER PUBLICATIONS

German Office Action for German Application No. 10-2016-223-490.0 dated Jul. 26, 2017.

*Primary Examiner* — David P Porta
*Assistant Examiner* — Fani Boosalis
(74) *Attorney, Agent, or Firm* — Harness, Dickey & Pierce, P.L.C.

(57) ABSTRACT

A system includes a gantry of a medical imaging apparatus. In an embodiment, the gantry includes an X-ray source, and a radiation protection booth, which can be installed or suspended relative to the gantry.

22 Claims, 7 Drawing Sheets

(51) Int. Cl.
*A61B 34/30* (2016.01)
*A61B 17/32* (2006.01)
*A61B 17/3211* (2006.01)
*A61N 5/10* (2006.01)

(56) References Cited

U.S. PATENT DOCUMENTS

| | | | |
|---|---|---|---|
| 7,112,811 B2 | 9/2006 | Lemer | |
| 7,591,590 B2* | 9/2009 | Cadwalader | A61B 6/107 |
| | | | 250/519.1 |
| 8,540,425 B2* | 9/2013 | Nielsen Groot | A61B 6/107 |
| | | | 378/203 |
| 2009/0110152 A1 | 4/2009 | Manzke | |
| 2011/0150177 A1* | 6/2011 | Nielsen Groot | A61B 6/107 |
| | | | 378/20 |
| 2014/0254745 A1* | 9/2014 | Nakai | A61B 6/463 |
| | | | 378/4 |
| 2016/0174914 A1 | 6/2016 | Lerch | |
| 2016/0296197 A1* | 10/2016 | Daum | A61B 6/547 |
| 2018/0000454 A1 | 1/2018 | Senn et al. | |
| 2018/0280733 A1* | 10/2018 | Weidlich | A61N 5/1081 |

FOREIGN PATENT DOCUMENTS

| | | |
|---|---|---|
| DE | 202016004185 U1 | 8/2016 |
| DE | 102016211902 A1 | 1/2018 |
| EP | 3229161 A2 | 10/2017 |
| KR | 101598972 B1 | 3/2016 |

\* cited by examiner

SYSTEM WITH A GANTRY AND A RADIATION PROTECTION BOOTH AND METHOD FOR OPERATING A MEDICAL IMAGING APPARATUS

PRIORITY STATEMENT

The present application hereby claims priority under 35 U.S.C. § 119 to German patent application number DE 102016223490.0 filed Nov. 25, 2016, the entire contents of which are hereby incorporated herein by reference.

FIELD

At least one embodiment of the invention generally relates to a system with a gantry and a radiation protection booth; a method for operating a medical imaging apparatus; a method for outputting a movement drive signal to a movement drive unit of a movable radiation protection booth and/or a method for moving a movable gantry and a movable radiation protection booth.

BACKGROUND

For reasons of patient proximity and patient safety, during an examination or image-guided therapy, it can be advantageous for a user, in particular medical staff, to be able to remain close to the medical imaging apparatus. However, it is also important to minimize risks to the health of the user, in particular due to X-rays. Patient proximity can have a direct effect on the comfort of conscious, cooperative patients making them more cooperative and hence achieving better examination results and patient satisfaction. This also increases patient compliance, for example in the case of breathing commands, restrictions of movement, calming agitating patients or the like. In addition, patient proximity can result in better control of patients who are sedated, anesthetized or uncooperative or patients in a potentially fatal condition.

Not only radiologists, but also physicians in other specialized disciplines can benefit from patient proximity, for example an anesthetist in the case of intensive-care patients or patients with multiple injuries or an internal specialist or surgeon in emergencies. One possibility for a user to establish patient proximity is based on the use of a radiation protection vest, but this can only partially protect the user. As a rule, due to the exposure to radiation, such protection is only used if there are special reasons, for example in the case of children and/or high-risk interventions. Otherwise, in many cases the user is required to leave the examination chamber in which the medical imaging apparatus is located before the initiation of the radiation for the acquisition of imaging data and remain, for example, in a control room protected against ionizing radiation from which the medical imaging apparatus can be operated.

SUMMARY

At least one embodiment of the invention provides an alternative possibility for operating a medical imaging apparatus.

The claims consider further advantageous embodiments of the invention.

At least one embodiment of the invention relates to a system comprising
a gantry of a medical imaging apparatus, the gantry including an X-ray source; and
a radiation protection booth, wherein the radiation protection booth can be installed, in particular is installed in at least one operating condition of the system, or suspended, in particular is suspended in at least one operating condition of the system, relative to the gantry.

At least one embodiment of the invention further relates to a method for operating a medical imaging apparatus, the method comprising:
execution of a first action of a user for operating the medical imaging apparatus, wherein the user is located inside an examination chamber and outside a radiation protection booth, wherein the radiation protection booth and a gantry of the medical imaging apparatus are located inside the examination chamber,
entry of the user into the radiation protection booth, and
execution of a second action of the user for operating the medical imaging apparatus, wherein the user is located inside the radiation protection booth.

At least one embodiment of the invention further relates to a method for outputting a movement drive signal to a movement drive unit of a movable radiation protection booth, the method comprising:
provision of position information relating to a gantry of a medical imaging apparatus, and
outputting the movement drive signal to the movement drive unit of the movable radiation protection booth based on the position information.

At least one embodiment of the invention further relates to a method for moving a movable gantry and a movable radiation protection booth, the method comprising:
moving a movable gantry,
provision of position information relating to the movable gantry of a medical imaging apparatus,
outputting the movement drive signal to the movement drive unit of the movable radiation protection booth based on the position information, and
moving the movable radiation protection booth via the movement drive unit based on the movement drive signal.

BRIEF DESCRIPTION OF THE DRAWINGS

Selected embodiments are explained below with reference to the attached figures. The representation in the figures is schematic, greatly simplified and not necessarily true-to-scale.

The figures show.

DETAILED DESCRIPTION OF THE EXAMPLE EMBODIMENTS

Figure 1:
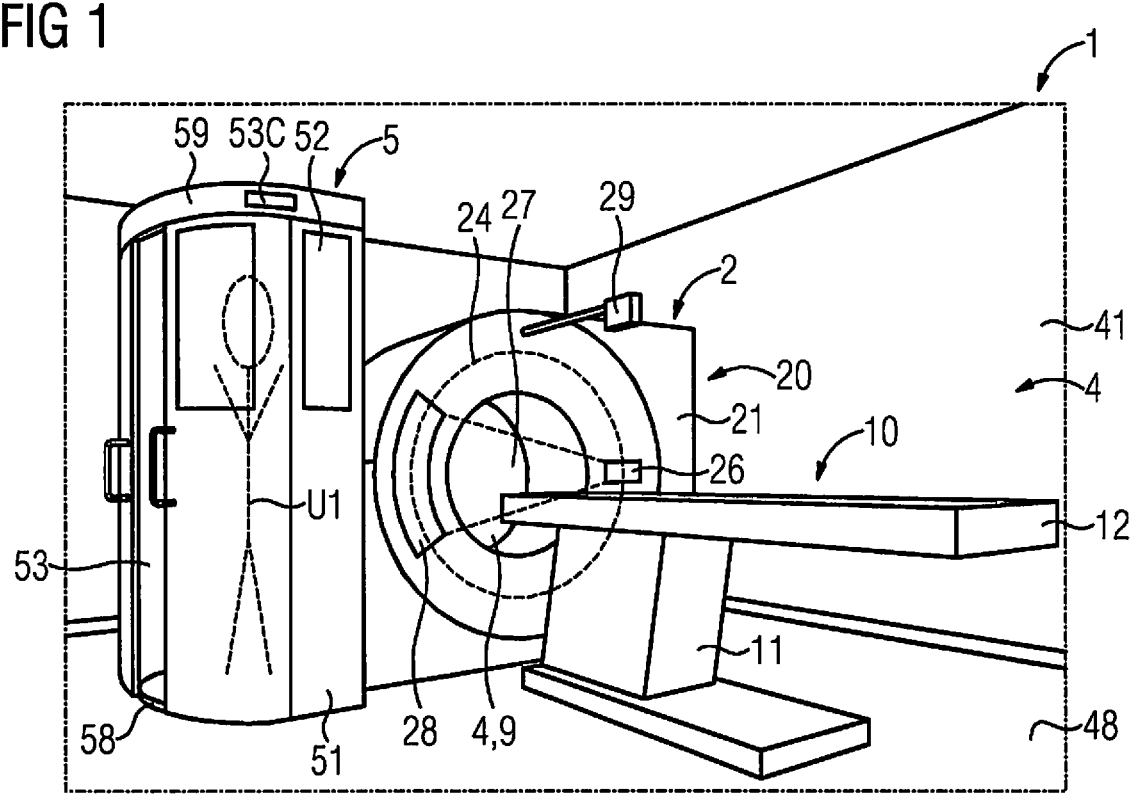
FIG. 1 a system according to one embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a system comprising
 a gantry of a medical imaging apparatus, the gantry including an X-ray source; and
 a radiation protection booth, wherein the radiation protection booth can be installed, in particular is installed in at least one operating condition of the system, or suspended, in particular is suspended in at least one operating condition of the system, relative to the gantry.

According to at least one embodiment of the invention, a system is provided
 wherein the maximum extension of the radiation protection booth in a first horizontal direction is less than 2 meters, in particular less than 1.5 meters, in particular less than 1 meter and/or
 wherein the maximum extension of the radiation protection booth in a second horizontal direction, which is perpendicular to the first horizontal direction, is less than 2 meters, in particular less than 1.5 meters, in particular less than 1 meter.

According to at least one embodiment of the invention, a system is provided further comprising an examination chamber, wherein the gantry and the radiation protection booth are located in the examination chamber.

According to at least one embodiment of the invention, a system is provided further comprising a user interface for operating the medical imaging apparatus, wherein the user interface can be arranged, in particular is arranged in at least one operating condition of the system, in the radiation protection booth.

According to at least one embodiment of the invention, a system is provided
 wherein the user interface comprises a tablet computer and/or a smartphone with a software application embodied to control the medical imaging apparatus and/or
 wherein the first user interface comprises a mobile control device with an operating element embodied as an electromechanical switching element.

According to at least one embodiment of the invention, a system is provided further comprising a data transfer unit embodied to transfer signals into the radiation protection booth and/or out of the radiation protection booth.

According to at least one embodiment of the invention, a system is provided, further comprising
 a door control unit embodied to control a door of the radiation protection booth based on information relating to a position of a user and/or a status of a medical workflow.

According to at least one embodiment of the invention, a system is provided further comprising a patient support apparatus of the medical imaging apparatus, which comprises a supporting base and a transfer plate arranged movably on the supporting base, which can be introduced into a tunnel-shaped opening in the gantry.

The system can in particular comprise the medical imaging apparatus.

According to at least one embodiment of the invention, a system is provided further comprising a camera arranged to acquire at least one region of the tunnel-shaped opening and/or at least one region of a transfer plate.

According to at least one embodiment of the invention, a system is provided further comprising at least one chassis for movably supporting the gantry and/or the radiation protection booth.

According to at least one embodiment of the invention, a system is provided further comprising at least one rail arrangement for movably supporting the gantry and/or the radiation protection booth.

According to at least one embodiment of the invention, a system is provided further comprising an intervention module for operating an intervention robot, wherein the intervention module can be arranged in the radiation protection booth, and/or an intervention robot.

According to at least one embodiment of the invention, a system is provided further comprising a therapeutic apparatus, which is based on beams and/or on particles.

At least one embodiment of the invention further relates to a method for operating a medical imaging apparatus, the method comprising:

execution of a first action of a user for operating the medical imaging apparatus, wherein the user is located inside an examination chamber and outside a radiation protection booth, wherein the radiation protection booth and a gantry of the medical imaging apparatus are located inside the examination chamber, entry of the user into the radiation protection booth, and execution of a second action of the user for operating the medical imaging apparatus, wherein the user is located inside the radiation protection booth.

At least one embodiment of the invention further relates to a method for outputting a movement drive signal to a movement drive unit of a movable radiation protection booth, the method comprising:

provision of position information relating to a gantry of a medical imaging apparatus, and outputting the movement drive signal to the movement drive unit of the movable radiation protection booth based on the position information.

At least one embodiment of the invention further relates to a method for moving a movable gantry and a movable radiation protection booth, the method comprising:

moving a movable gantry, provision of position information relating to the movable gantry of a medical imaging apparatus, outputting the movement drive signal to the movement drive unit of the movable radiation protection booth based on the position information, and moving the movable radiation protection booth via the movement drive unit based on the movement drive signal.

The radiation protection booth can in particular be installed or suspended relative to the gantry without thereby the dimensions of the radiation protection booth being changed and/or without thereby a volume of the radiation protection booth being changed and/or without thereby a circumference of the radiation protection booth, in particular in a horizontal plane, being changed.

The radiation protection booth can in particular be installed or suspended inside an examination chamber. In particular, herein a system is disclosed comprising a gantry of a medical imaging apparatus, wherein the gantry comprises an X-ray source, and a radiation protection booth, wherein the radiation protection booth can be installed or suspended inside an examination chamber. The examination chamber can in particular be a medical examination chamber. The radiation protection booth can in particular be installed or suspended as a whole relative to the gantry and/or inside the examination chamber.

The radiation protection booth can in particular have a maximum horizontal cross-sectional area, which, for example, is less than four square meters, in particular less than three square meters, in particular less than two square meters.

The relatively small dimensions of the radiation protection booth are associated with a reduced space requirement for the radiation protection booth inside the examination chamber, in particular in the vicinity of the gantry.

The radiation protection booth can in particular be detachably connectable or connected to a supporting structure. In particular, it can be provided that the supporting structure is a floor, a wall or a ceiling of the examination chamber and/or that the supporting structure is connected to a floor and/or to a wall and/or to a ceiling of the examination chamber. The supporting structure can, for example, be embodied to absorb forces and/or moments acting on the radiation protection booth and relay them to a floor and/or a wall and/or a ceiling of the examination chamber. In particular, a radiation protection area, which is in particular protected against ionizing radiation from the X-ray source of the gantry, can be located inside the radiation protection booth. The radiation protection booth can in particular have a closed circumference, in particular a closed circumference in a horizontal plane.

In particular in at least one operating condition of the radiation protection booth, the radiation protection booth can comprise a first wall region and a second wall region, wherein the first wall region and the second wall region are in each case embodied to protect against ionizing radiation, in particular to attenuate ionizing radiation. In particular in at least one operating condition of the radiation protection booth, the radiation protection booth can comprise a third wall region and a fourth wall region, wherein the third wall region and the fourth wall region are in each case embodied to protect against ionizing radiation, in particular to attenuate ionizing radiation.

In particular, the first wall region and the second wall region can be located opposite one another, in particular located opposite one another with respect to a first horizontal direction. In particular, the third wall region and the fourth wall region can be located opposite one another, in particular located opposite one another with respect to a second horizontal direction that is perpendicular to the first horizontal direction.

In particular, the first wall region can be located between the third wall region and the fourth wall region, in particular located with respect to a circumference of the radiation protection booth in a horizontal plane between the third wall region and the fourth wall region. In particular, the second wall region can be located between the third wall region and the fourth wall region, in particular located with respect to a circumference of the radiation protection booth in a horizontal plane between the third wall region and the fourth wall region.

In particular, the third wall region can be located between the first wall region and the second wall region, in particular located with respect to a circumference of the radiation protection booth in a horizontal plane between the first wall region and the second wall region. In particular, the fourth wall region can be located between the first wall region and the second wall region, in particular located with respect to a circumference of the radiation protection booth in a horizontal plane between the first wall region and the second wall region.

In at least one operating condition of the radiation protection booth, the radiation protection booth can in particular comprise for each horizontal direction at least one wall region, which is embodied to protect against ionizing radiation, in particular to attenuate ionizing radiation coming from the respective horizontal direction and directed at a radiation protection area inside the radiation protection. This enables a person located in the radiation protection booth to be protected against ionizing radiation, and hence in particular against scattered radiation, along a closed circumference extending circumferentially in a horizontal plane.

In particular in at least one operating condition of the radiation protection booth, the radiation protection booth can comprise for each direction at least one wall region and/or at least one ceiling region and/or at least one floor region, which is embodied to protect against ionizing radiation, in particular to attenuate ionizing radiation coming from the respective horizontal direction and directed at a radiation protection area inside the radiation protection booth. This enables a person located in the radiation protection booth to be comprehensively protected against ionizing radiation and hence in particular against scattered radiation.

In particular in at least one operating condition of the radiation protection booth, the radiation protection area can be located between two opposing wall regions of the radiation protection booth each of which is embodied to protect against ionizing radiation, in particular to attenuate ionizing radiation. The radiation protection area can in particular be located between the first wall region of the radiation protection booth and the second wall region of the radiation protection booth. The radiation protection area can in particular be located between the third wall region of the radiation protection booth and the fourth wall region of the radiation protection booth.

In at least one operating condition of the radiation protection booth, the radiation protection area can in particular be screened with respect to each horizontal direction by a wall region of the radiation protection booth, which is embodied to protect against ionizing radiation, in particular to attenuate ionizing radiation. The radiation protection area can in particular be screened at the top by a ceiling region of the radiation protection booth and/or at the bottom by a floor region of the radiation protection booth, wherein the ceiling region and/or the floor region are in each case embodied to protect against ionizing radiation, in particular to attenuate ionizing radiation.

In at least one operating condition of the radiation protection booth, the radiation protection area can in particular be screened with respect to each direction by a wall region and/or by a ceiling region and/or by a floor region of the radiation protection booth, which is embodied to protect against ionizing radiation, in particular to attenuate ionizing radiation. The radiation protection area can in particular be embodied such that at least one person can be present in the radiation protection booth, for example standing and/or sitting, and/or can use a user interface to operate the medical imaging apparatus and/or an intervention robot.

In at least one operating condition of the radiation protection booth, the radiation protection booth can in particular be embodied such that the radiation protection booth is embodied as airtight and/or watertight. The radiation protection booth can in particular comprise a breathing air filtering apparatus and/or a breathing air supply facility, for example with a breathing air reservoir, in particular an oxygen reservoir.

In particular during the acquisition of imaging data, in particular when the X-ray source is emitting radiation for the acquisition of imaging data, the solution according to at least one embodiment of the invention enables a user of the medical imaging apparatus to be present inside the examination chamber, in particular in the vicinity of a patient examined by way of the medical imaging apparatus. Herein the user located inside the radiation protection booth can also be protected from scattered radiation from all directions via the radiation protection booth. As a result of scattering of the radiation emitted directly by the X-ray source, the scattered radiation can occur on objects located inside the examination chamber and/or on a wall, a floor and/or a ceiling of the examination chamber. A floor can in particular also be understood to mean a floor underlay, floor plate or the like.

The proximity to the patient enables the associated advantages, which are in particular described above, to be achieved without the user being exposed to an increased radiation risk. Moreover, reducing the travel distances for the user, in particular to radiation-protected areas outside the examination chamber, can also increase examination workflow efficiency. Herein, the increased efficiency is not at the expense of human attention and patient comfort, instead it has a positive effect thereupon.

Particular medical advantages are, for example, obtained in the case of emergency patients. If, during the emission of the radiation in the radiation protection booth, the user is able to remain in the exposure area of the in particular critically unstable patient, not only is the user able more quickly to recognize a deterioration in the patient's condition and the need for intervention, the spatial proximity also enables more rapid intervention. Both embodiments mean seconds, which, in case of doubt, can mean the difference between life and death.

Moreover, while present in the radiation protection booth, the user is better able to control and monitor devices and/or monitors located inside the examination chamber, in particular outside the radiation protection booth. In the case of supervised patients, for example children or in dementia cases, key individuals can be present in the vicinity of the patient without additional radiation exposure. Due to the calming effect this has on the patient, this can improve image quality, in particular due to a reduction in motion artifacts, or even render the examination possible in the first place.

The radiation protection booth can in particular be located inside a circumscribed circle of 4 meters, in particular 3 meters, in particular 2 meters, around the isocenter of the gantry and/or the medical imaging apparatus.

The user interface can, for example, comprise a screen and/or a mouse and/or a keyboard. The user interface can, for example, be connected to a computer for operating the medical imaging apparatus, which is located inside the radiation protection booth and/or outside the radiation protection booth. The user interface can, for example, comprise a mobile user interface and/or a touch-sensitive screen.

In particular, there can be a holder and/or at least one docking station for the user interface inside the radiation protection booth, in particular inside the radiation protection area. The at least one docking station can, for example, be embodied for the detachable docking of the user interface, in particular the tablet computer and/or the mobile control device, and/or for the power supply for the user interface and/or for data transfer to the user interface and/or from the user interface. The docking station can, for example, comprise a magnetic holder.

In at least one operating condition of the system, the mobile control device and a control unit of a component of the medical imaging apparatus can be coupled such that actuating the operating element effects the output of a control signal to the component via the control unit. The component can, for example, be a transfer plate or a radiation source. The operating element can in particular be embodied as an electromechanical switching element if it comprises the electromechanical switching element.

The electromechanical switching element can in particular be a switch, for example a pushbutton. In many cases, an operating element embodied as an electromechanical switching element can achieve a higher level of safety, in particular with respect to movements of the transfer plate and the initiation of the radiation, than for example in the case of an operating element embedded in a software application. In particular, a further docking station can be provided, which is arranged on the gantry and which is embodied substantially the same as the docking station, which is located in radiation protection booth.

Both the tablet computer and the mobile control device can be taken into the radiation protection booth by the user and then taken out again, in particular docked on one of the docking stations inside or outside the radiation protection booth. This concept can enable the user to have full control of the medical imaging apparatus with maximum flexibility as to the location from which the user wishes to exercise the control.

The data transfer can, for example, be at least partially wireless and/or at least partially wired. The data transfer can, for example, be at least partially based on WLAN signals and/or Bluetooth signals. The radiation protection booth can in particular, at least in sections, be embodied as permeable to data transfer signals, in particular WLAN signals and/or Bluetooth signals and/or optical signals.

The radiation protection booth can in particular comprise a data transfer unit. The data transfer unit of the radiation protection booth can, for example, be embodied to receive a data transmission signal located outside the radiation protection booth, in particular in the examination chamber, and to make it available inside the radiation protection booth, in particular in the radiation protection area. The data transfer unit of the radiation protection booth can in particular comprise modules for receiving and/or transmitting data transmission signals, for example WLAN signals or Bluetooth signals. The data transfer unit of the radiation protection booth can, for example, comprise wired data transfer paths, for example to the docking station inside the radiation protection booth.

The radiation protection booth can, for example, comprise a mechanism, which is in particular embodied for motorized opening and closing of the door of the radiation protection booth. The door control unit can be embodied in particular to control this mechanism. The door control unit can in particular be automated and/or interact with a control loop. This can simplify the workflow for the user to the extent that the user no longer has consciously to think about opening and/or closing the door of the radiation protection booth. The opening and/or closing of the door of the radiation protection booth can also take place automatically if the user has no free hand, is wearing sterile protective clothing and/or sterile gloves and/or is distracted.

For example, it can be provided that the door closes automatically when the emission of the radiation is released and/or that the door automatically opens when the emission of the radiation is completed. The door control unit can, for example, comprise an emergency opening apparatus and/or an anti-crush apparatus or the like. Alternatively or additionally, the door can also be operated via a foot switch arrangement.

The camera can in particular be arranged on the gantry and/or on the radiation protection booth. In particular, the camera can be arranged such that at least one region of the tunnel-shaped opening and/or at least one region of the transfer plate that is not visible to a user located in the radiation protection booth is acquired. A camera image taken by the camera can, for example, be output via the user interface, for example via the tablet computer, and/or via a screen arranged inside the radiation protection booth.

The chassis can in particular be an omnidirectional chassis and/or a set of wheels, in particular omnidirectional wheels.

The radiation protection booth can, for example, be coupled mechanically to the gantry, in particular coupled such that the gantry and the radiation protection booth can only be moved together. According to one embodiment of the invention, the radiation protection booth can be pulled or pushed via the gantry.

The system can, for example, comprise a gantry-drive unit for driving a movement of the gantry and/or a radiation protection booth-drive unit for driving a movement of the radiation protection booth. The gantry-drive unit can, for example, comprise a motor, in particular an electric motor, and/or a corresponding power supply unit. The radiation protection booth-drive unit can, for example, comprise a motor, in particular an electric motor, and/or a corresponding power supply unit. The gantry-drive unit can, for example, be integrated in the gantry and/or in a rail arrangement. The radiation protection booth-drive unit can, for example, be integrated in the radiation protection booth and/or in a rail arrangement.

The position information can, for example, be used to acquire a changed position and/or movement of the gantry. In particular, it is possible for the radiation protection booth to be moved when the user is located in the radiation protection booth. In particular, a movement control unit can be located inside the radiation protection booth with which the user can control the movement of the radiation protection booth. In particular, the user interface can be embodied to control the movement of the radiation protection booth. The position information can, for example, be at least partially provided via a sensor arrangement arranged, for example, in the examination chamber, in particular on the radiation protection booth and/or on the gantry.

The sensor arrangement can, for example, comprise optical sensors and/or a camera and/or sensors on the gantry-drive unit. The position information can, for example, be at least partially provided and/or processed via a control apparatus of the medical imaging apparatus. The position information can in particular also be movement information and/or position change information. This in particular enables the implementation of synchronized movement of the gantry and the radiation protection booth.

An intervention robot can in particular also be understood to be a surgical robot. The intervention robot can, for example, be used to perform an intervention on a patient while the patient is located on the transfer plate. To monitor and/or adapt the intervention, the medical imaging apparatus can be used to record medical images, in particular tomography images, of the region of the patient in which the intervention is performed. The intervention robot can, for example, introduce needles and/or probes into the patient along a preplanned trajectory. The surgical robot can, for example, in particular introduce an endoscopic scalpel remotely. In particular, the intervention robot can be controlled by the user using the intervention module, wherein the user is located in the radiation protection booth.

Interventions are often performed on conscious patients, which simultaneously requires that the procedure be terminated rapidly and the patient be kept calm. Reducing the travel distances for the user and the time spent by the user in the vicinity of the patient can have a positive effect on these factors. Both are facilitated by the solution according to at least one embodiment of the invention. In particular, the system can comprise a movable gantry, a movable radiation protection booth and/or an intervention robot. This is in particular advantageous in the case of complex surgical scenarios with special patient support apparatuses.

The user interface can in particular comprise the intervention module. In particular, a docking station for docking the intervention module can be arranged in the radiation protection booth. The user interface can in particular be embodied to operate the patient support apparatus and/or to operate the radiation source and/or to operate the medical imaging apparatus via a software application and/or to operate the intervention robot.

The therapeutic apparatus can in particular be embodied for image-guided radiation therapy based on at least one medical image recorded via the medical imaging apparatus. The examination chamber can, for example, be a radiation bunker in a particle or radiation therapy system. In particular in the case of radiation therapy linacs, increased scattered radiation can occur and these can also have a negative impact on the hardware of the medical imaging apparatus. Not only the user, but also as many components as possible of the medical imaging apparatus have to be protected from such radiation.

The solution according to at least one embodiment of the invention dispenses with the need for complicated cabling emerging from the radiation protection bunker for the accommodation of console workstations in a radiation-protected area outside the radiation bunker. A solution of this kind can be significantly simpler, cheaper and longer lasting. The radiation protection booth can in particular be embodied to protect against radiation from the therapeutic apparatus used for therapy, in particular against scattered radiation from the therapeutic apparatus. The user interface can in particular be embodied to control the therapeutic apparatus.

The medical imaging apparatus can, for example, be selected from the group of imaging modalities including an X-ray device, a C-arm X-ray device, which can in particular be mobile, a computed tomography device (CT device), a molecular imaging device (MI device), a single-photon emission computer tomography device (SPECT device), a positron emission tomography device (PET device), a magnetic resonance tomography device (MR device) and combinations thereof (in particular PET-CT device, PET-MR device, SPECT-CT device). The medical imaging apparatus can further comprise a combination of an imaging modality, selected, for example, from the imaging modality group and a radiation modality. Herein, the radiation modality can, for example, comprise a radiation unit for therapeutic radiation. Without restricting the general concept of the invention, for some of the embodiments, a computed tomography device is named as an example of a medical imaging apparatus.

According to one embodiment of the invention, the medical imaging apparatus comprises an acquisition unit embodied to acquire the imaging data. The acquisition unit can in particular comprise a radiation source and a radiation detector. One embodiment of the invention provides that the radiation source is embodied for the emission and/or excitation of radiation, in particular electromagnetic radiation, and/or that the radiation detector is embodied to detect the radiation, in particular the electromagnetic radiation. The radiation can, for example, travel from the radiation source to the region to be depicted and/or, following interaction with the region to be depicted, to the radiation detector. During interaction with the region to be depicted, the radiation is modified and hence becomes a carrier of information relating to the region to be depicted. During interaction of the radiation with the detector, this information is acquired in the form of imaging data.

In particular in the case of a computed tomography device and in the case of a C-arm X-ray device, the imaging data can be projection data, the acquisition unit a projection data-acquisition unit, the radiation source an X-ray source, the radiation detector a X-ray detector. The X-ray detector can in particular be a quantum-counting and/or energy-resolving X-ray detector.

The gantry of a medical imaging apparatus typically comprises a supporting structure on which in particular components of the acquisition unit, in particular the radiation source and/or the radiation detector, are arranged. The supporting structure of the gantry is typically sufficiently rigid and strong to ensure that the components of the acquisition unit can be arranged in a geometry sufficiently defined for the imaging both relative to one another and relative to a region to be depicted. In the case of a computed tomography device, the gantry typically comprises a support frame and a rotor supported pivotably relative to the support frame, wherein the radiation source and the radiation detector are arranged on the rotor. The gantry can optionally comprise a tilt frame supported tiltably relative to the support frame, wherein the rotor is arranged on the tilt frame.

In the case of a C-arm X-ray device, the gantry typically comprises a support frame and a C-arm supported swivelably relative to the support frame, wherein the radiation source and the radiation detector are arranged on the C-arm.

The system can, for example, comprise one or more components in the form of hardware and/or one or more components in the form of software. The hardware can, for example, interact with software and/or be configured via software. The software can, for example, be executed via the hardware.

The hardware can, for example, be a storage system, an FPGA system (field-programmable gate array), an ASIC system (application-specific integrated circuit), a microcontroller system, a processor system and combinations thereof. The processor system can, for example, comprise a microprocessor and/or a plurality of interacting microprocessors.

In particular, a component of a system according to one of the embodiments disclosed in this description and/or in the claims, which is embodied to carry out a given step of a method according to one of the embodiments disclosed in this description and/or in the claims, can be implemented in the form of hardware configured to execute the given step and/or configured to execute a computer-readable instruction such that the hardware can be configured via the computer-readable instruction to execute the given step. In particular, the system can comprise a storage area, for example in the form of a computer-readable medium, in which computer-readable instructions are stored, for example in the form of a computer program.

A data transfer between components of the system can, for example, in each case take place via a suitable data-transfer interface. The data-transfer interface for data transfer to and/or from a component of the data-processing system can be implemented at least partially in the form of software and/or at least partially in the form of hardware. The data-transfer interface can, for example, be embodied to store data in and/or to load data from a region of the memory system, wherein one or more components of the data-processing can access this region of the memory system.

Within the scope of the invention, features described with respect to different embodiments of the invention and/or different claim categories (method, use, apparatus, system, arrangement etc.) can be combined to form further embodiments of the invention. For example, a claim relating to an apparatus can also be developed with features described or claimed in conjunction with a method. Herein, functional features of a method can be implemented by correspondingly embodied material components. In addition to the embodiments of the invention expressly described in this application, numerous further embodiments of the invention are conceivable at which the person skilled in the art can arrive without departing from the scope of the invention in so far as it is defined by the claims.

The use of the indefinite article "a" or "an" does not precludes the possibility of the features in question also being present on a multiple basis. The use of the expression "comprise" does not preclude the possibility of the terms being linked by the expression "comprise" being identical. For example, the medical imaging apparatus comprises the medical imaging apparatus. The use of the expression "unit" does not exclude the possibility of the subject matter to which the expression "unit" relates comprising a plurality of components that are spatially separated from one another.

In the context of the present application, the use of ordinal numbers (first, second, third etc.) in the description of features is primarily for better distinction of those features described using ordinal numbers. The absence of a feature described by a combination of a given ordinal number and a term does not preclude the possibility of a feature being present that is also described by a combination of an ordinal number following the given ordinal numbers and said term.

In the context of the present application, the expression "based on" can particular be understood as meaning "using". In particular, wording according to which a first feature is created based on a second feature (alternatively: determined, identified etc.) does not preclude the possibility of the first feature being created based on a third feature (alternatively: determined, identified etc.).

The use of a feature in the form "wherein for each dataset of the plurality of datasets a result is determined in each case" does not preclude the possibility that, in addition to the datasets included in the plurality of datasets, further datasets can be present, which are not included in the plurality of datasets and for which the result is not determined. In particular, the plurality of datasets can be a subset of a set of datasets, wherein the set of datasets also comprises datasets, which are included in the plurality of datasets and for which the result is determined in each case, and also datasets, which are not included in the plurality of datasets and for which the result is not determined.

FIG. 1 shows a system 1 according to one embodiment of the invention. In FIG. 1, the radiation protection booth 5 is arranged next to the gantry 20 such that a large part of the radiation is attenuated by the gantry itself before it reaches the radiation protection booth. The radiation protection booth 5 is located inside the examination chamber 4. The examination chamber 4 comprises walls 41 and a floor 48. The radiation protection booth 5 comprises leaded glass panes 52. Through the leaded glass panes, a user U1 located inside the radiation protection booth can see at least a part of the patient 13. The walls 51 of the radiation protection booth are at least partially lined with lead. In particular, the walls 51 of the radiation protection booth can comprise a lead-lined light skeleton construction, for example based on wood, aluminum or plastic. As shown in FIG. 1, the radiation protection booth does not form a structural unit with the examination chamber. The radiation protection booth 5 comprises a floor 58 and a ceiling 59. However, the radiation protection booth 5 can also be embodied as open at the top and/or bottom and/or as bounded by a ceiling of the examination chamber 4 and/or by a floor of the examination chamber. The radiation protection booth comprises a door 53 and a door control unit 53C. A camera 29 is arranged on the gantry.

Without restricting of the general concept of embodiments of the invention, a computed tomography device is shown by way of example for the medical imaging apparatus 2. The medical imaging apparatus 2 comprises the gantry 20, the tunnel-shaped opening 9, the patient support apparatus 10 and the control apparatus 30.

The gantry 20 comprises the stationary support frame 21, the tilt frame and the rotor 24. The tilt frame is arranged via a tilting supporting apparatus on the stationary support frame 21 tiltably about a tilting axis relative to the stationary support frame 21. The rotor 24 is arranged via a pivoting support apparatus on the tilt frame pivotably about an axis of rotation relative to the tilt frame.

The tilting axis is perpendicular to the system axis. The system axis and the tilting axis are located in a horizontal plane. The axis of rotation is perpendicular to the tilting axis and substantially parallel to the system axis.

The patient 13 can be introduced into the tunnel-shaped opening 9. The acquisition region 4 is located in the tunnel-shaped opening 9. A region of the patient 13 to be depicted can be positioned in the acquisition region 4 such that the radiation 27 can travel from the radiation source 26 to the region to be depicted and, following interaction with the region to be depicted, travel to the radiation detector 28.

The patient support apparatus 10 comprises the supporting base 11 and the supporting plate 12 for supporting the patient 13. The supporting plate 12 is arranged movably relative to the supporting base 11 on the supporting base 11 such that the supporting plate 12 can be introduced into the acquisition region 4 in a longitudinal direction of the supporting plate 12, in particular along the system axis.

The medical imaging apparatus 2 is embodied for the acquisition of acquisition data based on electromagnetic radiation 27. The medical imaging apparatus 2 comprises an acquisition unit. The acquisition unit is a projection data-acquisition unit with the radiation source 26, for example a X-ray source, and the detector 28, for example a X-ray detector, in particular an energy-resolving X-ray detector. The radiation source 26 is arranged on the rotor 24 and embodied to emit radiation 27, for example X-rays, with radiation quanta 27. The detector 28 is arranged on the rotor 24 and embodied to detect the radiation quanta 27. The radiation quanta 27 can travel from the radiation source 26 to the region of the patient 13 to be depicted and, following interaction with the region to be depicted, strike the detector 28. This enables the acquisition unit to acquire acquisition data of the region to be depicted in the form of projection data.

The control apparatus 30 is embodied to receive the acquisition data acquired from the acquisition unit. The control apparatus 30 is embodied to control the medical imaging apparatus 2. The control apparatus 30 comprises the data-processing unit 35, a computer-readable medium and the processor system 36. The control apparatus 30, in particular the data-processing unit 35, is formed by a data-processing system comprising a computer.

The control apparatus 30 comprises the image reconstruction facility 34. The image reconstruction facility 34 can be used to reconstruct a medical image dataset based on the acquisition data.

The medical imaging apparatus 2 comprises an input apparatus and an output apparatus each of which is connected to the control apparatus 30. The input apparatus is embodied to input control information, for example image-reconstruction parameters, examination parameters or the like. The output apparatus is in particular embodied to output control information, images and/or acoustic signals.

Figure 2:
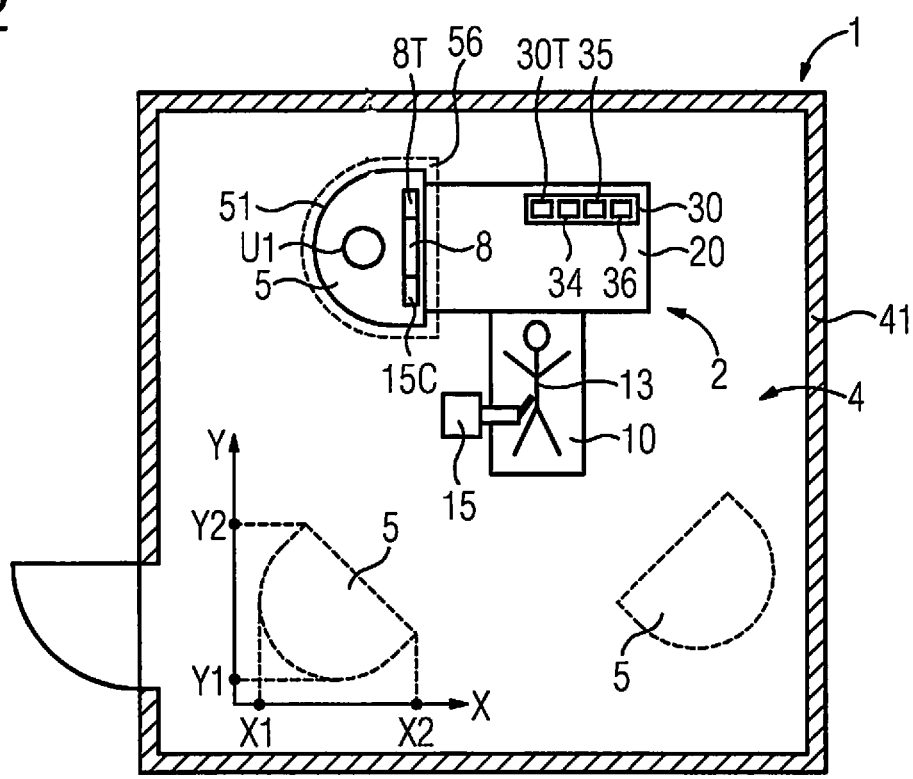
FIG. 2 a system according to a further embodiment of the invention.

As shown in FIG. 2, the examination chamber contains a border region 56 surrounding the radiation protection booth along a closed contour extending circumferentially in the horizontal plane. The system 1 comprises the user interface 8, the intervention module 15C, the intervention robot 15, the data transfer unit 8T of the user interface 8 and the data transfer unit 30T of the control apparatus 30. The control apparatus 30 is integrated in the gantry 20. This enables heat and the development of noise in the radiation protection booth to be avoided. Dashed lines depict further possible positions for the radiation protection booth 5 in the examination chamber.

The maximum extension of the radiation protection booth 5 in a first horizontal direction X is the distance between the points X1 and X2. The maximum extension of the radiation protection booth in a second horizontal direction Y, which is perpendicular to the first horizontal direction X, is the distance between the points Y1 and Y2.

Figure 3:
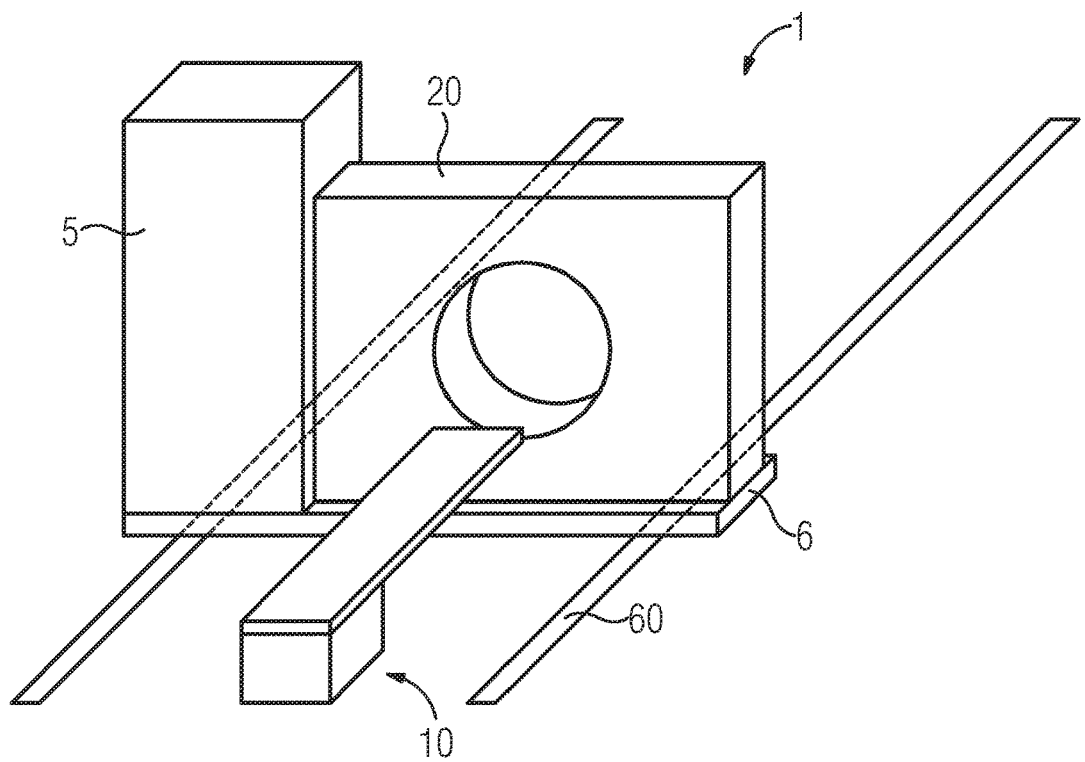
FIG. 3 a system according to a further embodiment of the invention.

The system depicted in FIG. 3 comprises a rail arrangement 60 for movably supporting the gantry 20 and the radiation protection booth 5. The gantry 20 and the radiation protection booth 5 are arranged on the platform 6, which can be moved via the rail arrangement 60.

Figure 4:
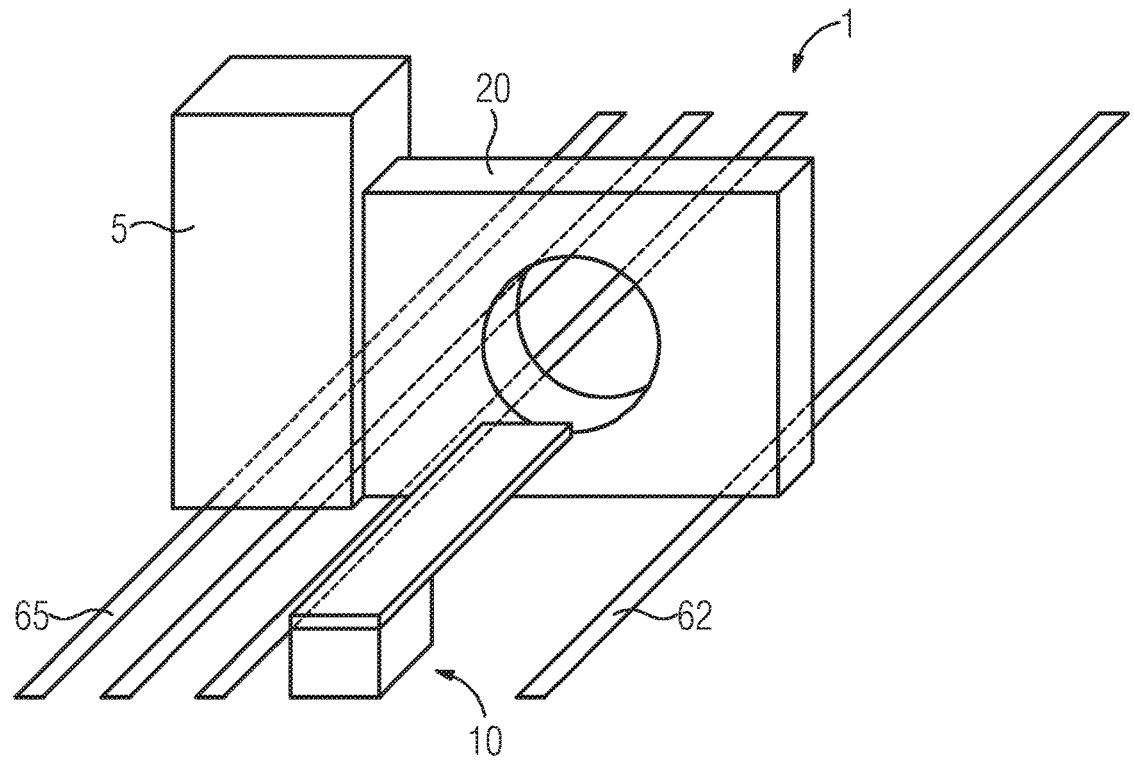
FIG. 4 a system according to a further embodiment of the invention.

The system depicted in FIG. 4 comprises a rail arrangement 62 for movably supporting the gantry 20 and a rail arrangement 65 for movably supporting the radiation protection booth 5.

Figure 5:
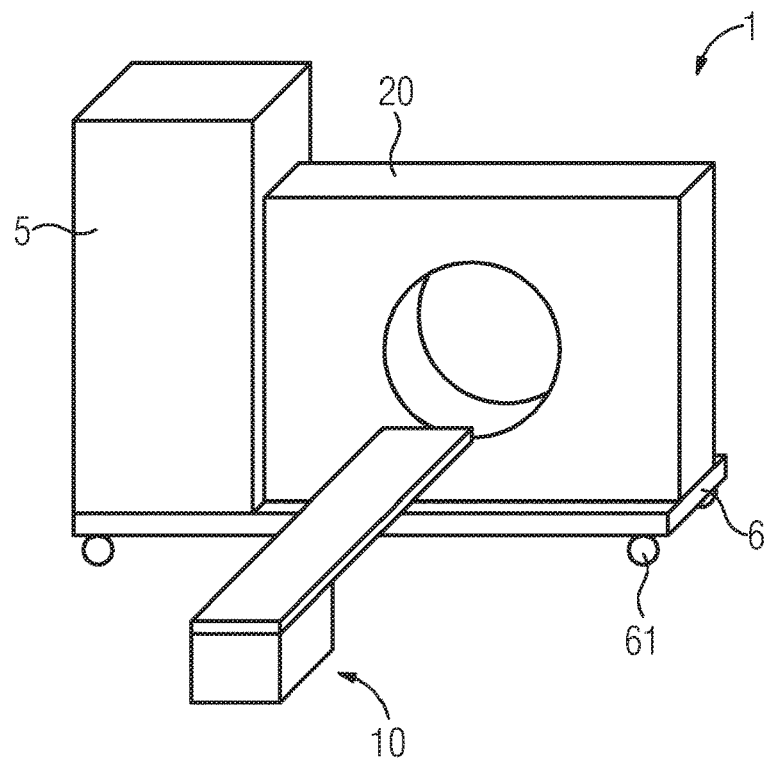
FIG. 5 a system according to a further embodiment of the invention.

The system depicted in FIG. 5 comprises a chassis 61 for movably supporting the gantry 20 and the radiation protection booth 5. The gantry 20 and the radiation protection booth 5 are arranged on the platform 6, which can be moved via the chassis 61.

Figure 6:
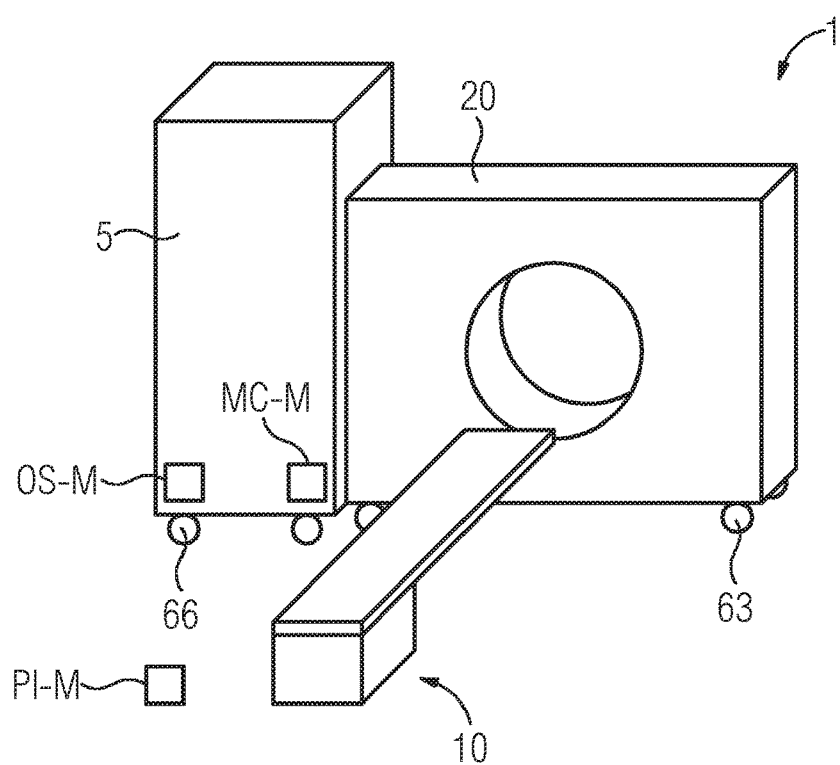
FIG. 6 a system according to a further embodiment of the invention.

The system depicted in FIG. 6 comprises a chassis 63 for movably supporting the gantry 20 and a chassis 66 for movably supporting the radiation protection booth 5. The system 1 further comprises a position-information-providing unit PI-M, for example in the form of a sensor arrangement embodied to provide position information relating to the movable gantry of a medical imaging apparatus. The system 1 further comprises a movement-drive-signal outputting unit OS-M embodied to output the movement drive signal to the movement drive unit of the movable radiation protection booth based on the position information. The movement drive signal output unit OS-M can, for example, comprise a processor unit and/or be formed by a data-processing system. The system further comprises a radiation protection booth-drive unit MC-M embodied to drive a movement of the radiation protection booth based on the movement drive signal.

Figure 7:
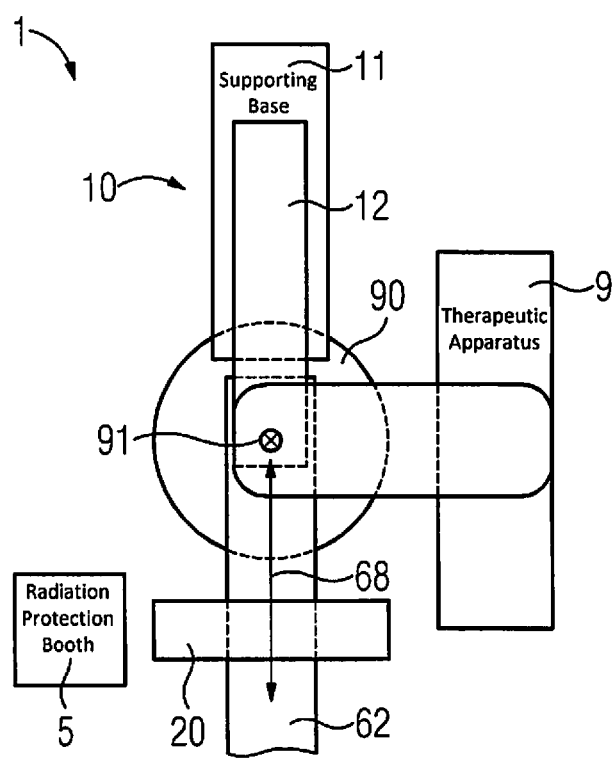
FIG. 7 a system according to a further embodiment of the invention.

The system shown in FIG. 7 comprises the therapeutic apparatus 9. The patient support apparatus 10 is pivotably supported about a vertical axis, which through the isocenter 91 of the medical imaging apparatus, which is also the isocenter of the therapeutic apparatus, via a pivotable floor plate 90. The gantry can be moved along the path 68 via the rail arrangement 62.

Figure 8:
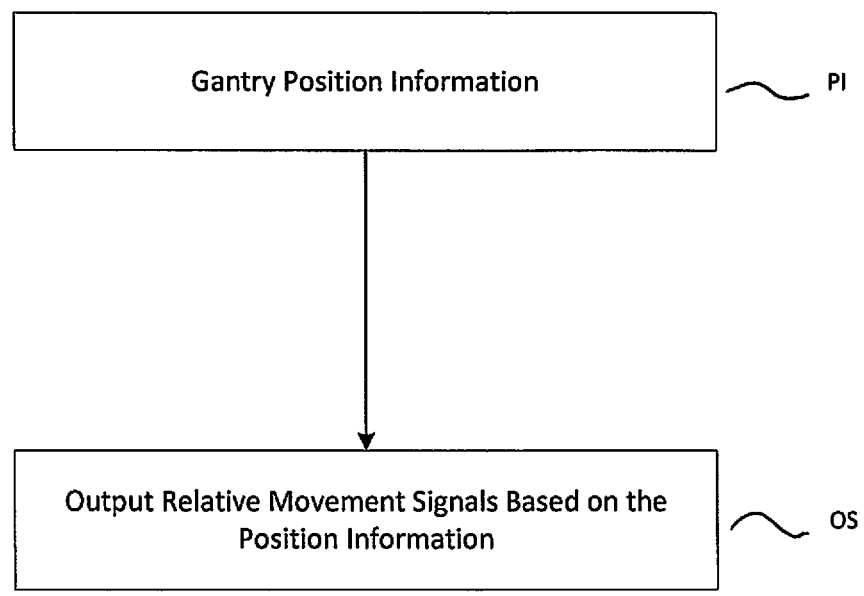
FIG. 8 a method according to one embodiment of the invention.

FIG. 8 shows the following steps:
provision PI of position information relating to a gantry of a medical imaging apparatus, and
outputting OS of the movement drive signal to the movement drive unit of the movable radiation protection booth based on the position information.

Figure 9:
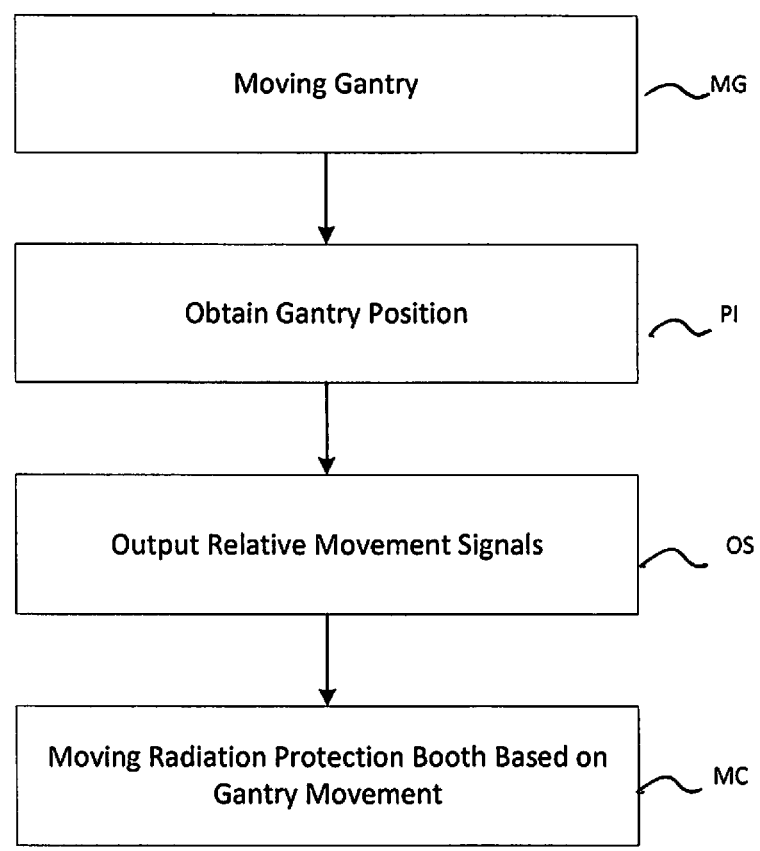
FIG. 9 a flowchart for a method according to one embodiment of the invention, and FIG. 10 a flowchart for a method according to one embodiment of the invention.

FIG. 9 further shows the following steps:
moving MG a movable gantry, and
moving MC the movable radiation protection booth via the movement drive unit based on the movement drive signal. The movement drive unit is in particular the radiation protection booth-drive unit.

Figure 10:
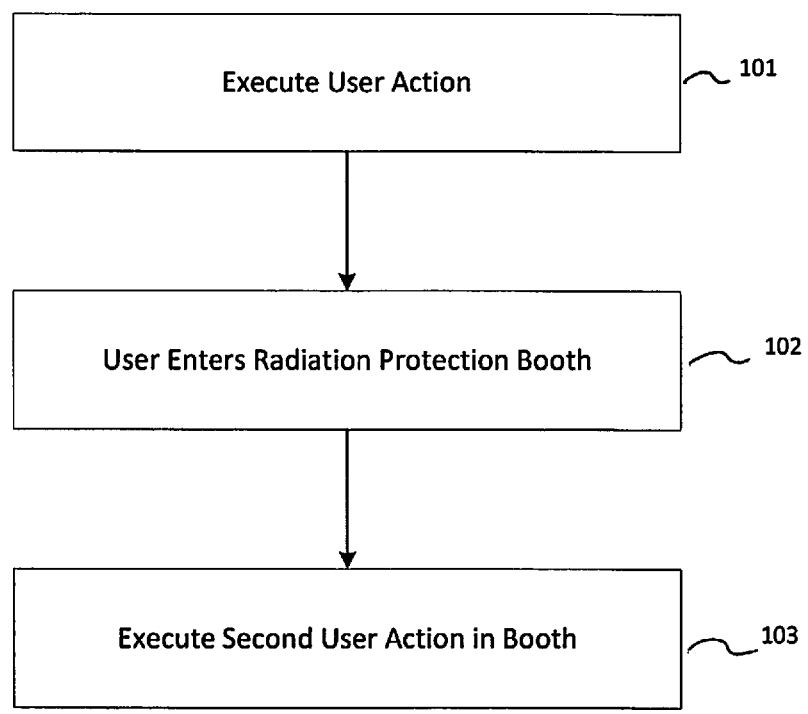

FIG. 10 shows the following steps:
execution 101 of a first action of a user for operating the medical imaging apparatus, wherein the user is located inside an examination chamber and outside a radiation protection booth, wherein the radiation protection booth and a gantry of the medical imaging apparatus are located inside the examination chamber,
entry 102 of the user into the radiation protection booth, and
execution 103 of a second action of the user for operating the medical imaging apparatus, wherein the user is located inside the radiation protection booth.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system comprising:
a gantry of a medical imaging apparatus, the gantry including an X-ray source;
a radiation protection booth having at least one wall surrounding a space into which a user may be enclosed, the radiation booth being installable or suspendable relative to the gantry; and
at least one of:
an intervention module for operating an intervention robot, wherein the intervention module is arrangeable in the radiation protection booth, and
an intervention robot.

2. The system of claim 1, wherein at least one of
a maximum extension of the radiation protection booth in a first horizontal direction is less than 2 meters; and
a maximum extension of the radiation protection booth in a second horizontal direction, perpendicular to the first horizontal direction, is less than 2 meters.

3. The system of claim 2, further comprising:
an examination chamber, wherein the gantry and the radiation protection booth are located in the examination chamber.

4. The system of claim 2, further comprising:
a user interface for operating the medical imaging apparatus, wherein the user interface is arrangable in the radiation protection booth.

5. The system of claim 1, further comprising:
an examination chamber, wherein the gantry and the radiation protection booth are located in the examination chamber.

6. The system of claim 5, further comprising:
at least one rail arrangement mounted to a floor of the examination chamber for movably supporting at least one of the gantry and the radiation protection booth.

7. The system of claim 5, further comprising:
a user interface for operating the medical imaging apparatus, wherein the user interface is arrangable in the radiation protection booth.

8. The system of claim 1, further comprising:
a user interface for operating the medical imaging apparatus, wherein the user interface is arrangable in the radiation protection booth.

9. The system of claim 8, wherein at least one of
the user interface comprises at least one of a tablet computer and a smartphone with a software application embodied to control the medical imaging apparatus, and
the user interface comprises a mobile control device with an operating element embodied as an electromechanical switching element.

10. The system of claim 1, further comprising:
a data transfer unit embodied to transfer signals at least one of into the radiation protection booth and out of the radiation protection booth.

11. The system of claim 1, further comprising:
a door in a wall of the radiation protection booth; and
a door control unit, embodied to control the door of the radiation protection booth based on information relating to at least one of a position of a user and a status of a medical workflow.

12. The system of claim 1, further comprising:
a patient support apparatus of the medical imaging apparatus including a supporting base and a transfer plate arranged movably on the supporting base, the transfer plate being introduceable into a tunnel-shaped opening the gantry.

13. The system of claim 12, further comprising:
a camera arranged to acquire at least one of at least one region of the tunnel-shaped opening and at least one region of a transfer plate.

14. The system of claim 1, further comprising:
at least one wheeled chassis for movably supporting at least one of the gantry and the radiation protection booth.

15. The system of claim 1, further comprising:
a therapeutic apparatus based on at least one of beams and particles.

16. The system of claim 1, wherein the radiation protection booth includes at least one leaded glass pane.

17. A method for operating a medical imaging apparatus, the method comprising:
executing a first action of a user for operating the medical imaging apparatus, the user being located inside an examination chamber and outside a radiation protection booth, wherein the radiation protection booth and a gantry of the medical imaging apparatus are located inside the examination chamber; and
executing a second action of the user for operating the medical imaging apparatus, the user moving to and being located inside the radiation protection booth before performing the executing of the second action.

18. A method for outputting a movement drive signal to a movement drive unit of a movable radiation protection booth, the method comprising:
provisioning position information relating to a gantry of a medical imaging apparatus; and
outputting the movement drive signal to the movement drive unit of the movable radiation protection booth based on the provisioned position information.

19. A method for moving a movable gantry and a movable radiation protection booth, the method comprising:
moving a movable gantry;
provisioning position information relating to the movable gantry of a medical imaging apparatus;

outputting a movement drive signal to a movement drive unit of the movable radiation protection booth based on the provisioned position information; and moving the movable radiation protection booth via the movement drive unit based on the output movement drive signal.

20. A system comprising:

a gantry of a medical imaging apparatus, the gantry including an X-ray source; and a radiation protection booth having at least one wall surrounding a space into which a user may be enclosed, the radiation booth being installable or suspendable relative to the gantry, wherein at least one of a maximum extension of the radiation protection booth in a first horizontal direction is less than 1.5 meters; and a maximum extension of the radiation protection booth in a second horizontal direction, perpendicular to the first horizontal direction, is less than 1.5 meters.

21. The system of claim 20, wherein at least one of a maximum extension of the radiation protection booth in a first horizontal direction is less than 1 meter; and a maximum extension of the radiation protection booth in a second horizontal direction, perpendicular to the first horizontal direction, is less than 1 meter.

22. A system comprising:

a gantry of a medical imaging apparatus, the gantry including an X-ray source; and a radiation protection booth having at least one wall surrounding a space that encloses an operator of the medical imaging apparatus while operating the medical imaging apparatus, the radiation booth being installable or suspendable relative to the gantry.

* * * * *